United States Patent [19]
Davis et al.

[11] Patent Number: 5,278,885
[45] Date of Patent: Jan. 11, 1994

[54] RUBBER PRODUCT IDENTIFICATION BY TAGGING

[75] Inventors: James A. Davis, Uniontown; Kenneth R. Lucas, Copley, both of Ohio

[73] Assignee: Bridgestone Corporation, Tokyo, Japan

[21] Appl. No.: 890,171

[22] Filed: May 29, 1992

Related U.S. Application Data

[62] Division of Ser. No. 602,543, Oct. 24, 1990, Pat. No. 5,145,750.

[51] Int. Cl.⁵ .......................................... G01N 23/223
[52] U.S. Cl. ...................................... 378/45; 378/210
[58] Field of Search ...................................... 378/45–49

[56] References Cited

U.S. PATENT DOCUMENTS 4,639,942  1/1987  Puumalainen ........................ 378/45

*Primary Examiner*—Craig E. Church
*Attorney, Agent, or Firm*—Frank J. Troy, Sr.

[57] ABSTRACT

The present invention provides a method for positive product identification using tagging materials such as barium sulfate, manganese dioxide or mixtures thereof. Such materials may be employed, for example, in the dusting agent used in roofing materials, and applied to one or both sides of rubber roofing sheeting or admixed with the compounding ingredients during the preparation of the sheeting composition. The tagging materials can be detected and identified in the finished product by X-ray fluorescence spectroscopy.

14 Claims, No Drawings

RUBBER PRODUCT IDENTIFICATION BY TAGGING

This is a divisional of copending application Ser. No. 07/602,543 filed on Oct. 24, 1990, now U.S. Pat. No. 5,145,750.

FIELD OF THE INVENTION

The present invention is directed to rubber product identification. More specifically, the present invention is directed to product identification by either incorporating certain amounts of a labelling material in the dusting or release agent which prevents the membrane from adhering to itself during steam curing or by directly adding an identifiable material to the membrane composition during the manufacturing of the membrane. The material can be easily identified using means such as X-ray fluorescence spectroscopy.

DESCRIPTION OF THE PRIOR ART

In recent years the construction of buildings, both commercial and residential, has increased dramatically. This increased construction spawns a corresponding rise in the need for construction products, such as roofing shingles.

As building purchasers become increasingly concerned with quality and workmanship, product warranties providing guarantees of quality and workmanship are in greater demand. As contractors cannot, however, directly control the material quality, they must rely on warranties offered by construction product manufacturers. Should any of these materials fail subsequent to construction, the building owner as well as the contractor must determine the source of the material. The manufacturer of the material must also be able to confirm that it is indeed the source of the defective material, as such identification is essential in the determination of liability for breach of warranty upon failure of the building materials.

Such failure or breach of warranty may also give rise to product liability litigation should the failure result in injury to person or property. In this situation as well, a correct determination of liability requires a means for identifying the manufacturer.

The ability to identify the manufacturer also serves other valuable functions in the building industry. First, it assists in the recovery of any stolen materials by providing means for identifying the source of the allegedly stolen property. Widespread knowledge of such capability may also provide a deterrent to theft. Further, such identification capability can assist the manufacturer in connection with internal inventory control and the monitoring of sales and use of the product. Also, the ability to identify the manufacturer of a defective product provides means for quickly and efficiently correcting latent defects prior to sale of a building.

In an attempt to address the need for identifying building products such as roofing shingles, U.S. Pat. No. 1,447,265 discloses a means for identifying prepared roofing including imbedding one or more identifiable threads in a coating applied to the roofing product. Threads of different colors and arranged in a variety of different combinations may be used to identify the various products either as to the time or place, or both, of origin.

While this method does generally provide a method for identifying roofing materials, it has a number of drawbacks when considered in view of more modern roofing materials. Initially, the inclusion of a thread in the roofing material requires a specific, additional manufacturing step, adding time and expense to the manufacturing process. Further, such threads may become separated from the roofing material, thereby destroying the ability to identify the roofing material. In addition, such imbedded threads are likely to disintegrate upon failure or destruction of the roofing material, thereby rendering identification impossible.

It is also known that "identification particles" are available from Microtrace, Inc. under the designation Microtaggants. Such particles comprise microscopic-sized plastic particles composed of distinct colored layers. The colors within the layers can be read by microscopic viewing at 100X magnification or viewed under UV light. It is believed that such particles are employed for identification purposes in paints, adhesives, coatings, possibly other roofing materials and the like.

However, the Microtaggant particles are not easily viewed or detectable when embedded in a rubber-based composition such as a roofing material, especially at low concentrations which are necessary in order for the Microtaggant particles to be cost effective, as visibility of such particles is orientation related. Such a disadvantage results from reliance upon visibility characteristics of the particles, which characteristics can be severely affected by inclusion of the particles within the roofing composition.

A need therefore exists for a method of identifying roofing materials that is inexpensive, efficient and able to withstand the long periods of continued exposure to which roofing material are subjected.

OBJECTS AND BRIEF SUMMARY OF THE INVENTION

It is thus an object of the present invention to provide a composition for a roofing membrane.

It is thus another object of the present invention to provide a composition for a roofing membrane which efficiently and effectively permits identification of various production parameters, including identification of the manufacturer, batch, date and time, etc.

It is yet another object of the present invention to provide a roofing membrane which includes a means for identifying various production parameters relating to the membrane.

It is still another object of the present invention to provide a method for producing a roofing membrane with means for identifying various production parameters relating to the membrane.

In accordance with the present invention, there is thus provided a roofing membrane composition comprised of a roofing material and an X-ray fluorescable material. The X-ray fluorescable material may be applied to the membrane as a coating layer (i.e., with a dusting agent) or admixed with the roofing membrane material prior to membrane formation. The membrane produced according to the present invention may be identified by irradiating the membrane which causes the X-ray fluorescable material to detectably fluoresce.

In accordance with the present invention, there is also provided an identifiable roofing material in sheet form, said sheet including over at least a portion of at least one surface thereof a coating comprised of an X-ray fluorescable material.

DESCRIPTION OF THE PREFERRED EMBODIMENTS

The roofing membrane of the present invention comprises a fluorescable labelling material and a conventional roofing membrane material.

Preferably, the membrane material is comprised of a material such as EPDM. The term "EPDM" is used in the sense of its definition as found in ASTM-D-1418-85 and is intended to denote a terpolymer of ethylene, propylene and a diene monomer. Such terpolymers are well-known and illustrative methods for preparing such terpolymers are found in U.S. Pat. No. 3,280,082 and British Patent No. 1,030,289, the disclosures of which are incorporated herein by reference. The preferred terpolymers contain from about 40 to about 80 weight percent ethylene and from about 1 to about 10 weight percent of the diene, with the balance of the terpolymer being propylene.

The diene monomer utilized in forming the EPDM terpolymer is preferably a non-conjugated diene. Illustrative examples of non-conjugated dienes which may be employed are dicyclopentadiene, alkyldicyclopentadiene, 1,4-pentadiene, 1,4-hexadiene, 1,5-hexadiene, 1,4-heptadiene, 2-methyl-1,5-hexadiene, cyclooctadiene, 1,4-octadiene, 1,7-octadiene, 5-ethylidene-2-norbornene, 5-n-propylidene-2-norbornene, 5-(2-methyl-2-butneyl)-2-norbornene and the like.

One suitable EPDM which may be used in the present invention is Vistalon 2504 (Exxon Chemical Co.), a terpolymer having a Mooney Viscosity (ML, 1+8, 1000° C.) of about 40 and having 50 weight percent of ethylene, 45 weight percent of propylene and 5.0 weight percent of 5-ethylidene-2-norbornene with an $\overline{M}_n$ as measured by GPC of about 47,000 and an $\overline{M}_w$ as measure by GPC of about 174,000. Another suitable EPDM is available from du Pont under the name Nordel 1070, an ethylene/propylene/1,4-hexadiene terpolymer having an $\overline{M}_n$ of about 87,000 and an $\overline{M}_w$ of about 188,000.

Neutralized sulfonated EPDM and butyl elastomers may also be employed in the compositions of the invention and are well known in the art. The preferred neutralized sulfonated elastomers are those having from about 10 to about 100, preferably from about 10 to about 30, milliequivalents (hereinafter meq) of neutralized sulfonate groups per 100 grams of elastomer. The term "neutralized" as used in the foregoing context is intended to encompass either complete neutralization of the sulfonate groups or partial neutralization of the sulfonate groups.

The EDPM or butyl elastomer can be sulfonated using a sulfonating agent selected from acetyl sulfate, propionyl sulfate and butyryl sulfate as described in U.S. Pat. No. 3,836,511, the disclosure of which is incorporated herein by reference.

The preferred neutralized sulfonated EPDM and butyl elastomers for use in the compositions of the invention are zinc neutralized sulfonated EPDM and butyl elastomers such as those described in U.S. Pat. Nos. 4,137,203 and 4,222,914, the disclosures of which are incorporated herein by reference. A particularly preferred zinc neutralized sulfonated EPDM elastomeric terpolymer for use in the compositions herein is a zinc sulfonated EPDM having a base EPDM molecular weight, $\overline{M}_n$, of about 50,000, an average number of $SO_3$-groups, a bulk density of 8-10 lbs./cu.ft., a Tg of $-60°$ C. and 25 meq of zinc sulfonate groups per 100 grams of terpolymer available under the designation IE-2590 from Uniroyal Chemical Company, Inc.

The roofing material may also be formed of other materials which are conventionally employed in roofing materials including but not limited to synthetic elastomers, such as neoprene, ethylene-propylene-diene monomers (EPDM), butyl, chlorosulfonated polyethylene (CSPE) or blends thereof. Also, thermoplastic elastomers, such as chlorinated polyethylene (CPE) and polyvinyl chloride (PVC) are occasionally utilized in some special applications.

The labelling material utilized in accordance with the present invention may be any material which X-ray fluoresces upon exposure to irradiation at a fluorescence-inducing wavelength.

Preferably, the utilized labelling materials are selected from the group consisting of barium sulfate and manganese dioxide. These materials are most preferably utilized in particulate or powdered form. The barium and magnesium elemental components of these labelling materials when irradiated with X-rays or an electron beam emit X-rays of characteristic energy or wavelength that uniquely identifies the presence of these elements. It is to be understood, however, that any combination of labelling materials and exciting radiation may be utilized during practice of the present invention, so long as the radiation utilized causes X-ray fluorescence of the labelling material.

By way of advantage, the use of identification particles such as barium sulfate and mangenese dioxide enable identification to be undertaken by means of chemical analysis for barium or manganese rather than by means of visible detection. As a result, the particle size of the identification particles is substantially immaterial and has substantially no effect upon the effectiveness of the identifying procedure.

In one embodiment of the membrane of the present invention, the labelling material is applied to a conventional roofing membrane in the form of a dust or dry powder. A majority of the dusting or release agent preferably comprises talc or mica. The labelling material most preferably comprises between about 5% and about 10% by weight of the total composition.

The addition of the labelling material to the dusting agent enables the roofing composition per se to be used without modification or inclusion of particles therein.

Such dusting or release agents are routinely employed in the manufacture of calendered rubber-based sheeting, such as roll goods, roofing membranes, pond liners, etc. The presence of barium sulfate or manganese dioxide within the dusting composition provides an effective and efficient means by which the product can be "tagged" for identification purposes.

In this embodiment, the roofing membrane of the present invention may be prepared in sheet form by conventional methods, such as calendering or extrusion with subsequent cutting of the sheet to desired dimensions, followed by the application of the fluorescable coating layer to one surface of the cut sheet. The application of the fluorescable dusting material to the cut sheet may occur by various methods such as slowly passing the calendered membrane through a dusting trough. Also, the dusting agent can be applied to one or both sides of the membrane by the use of fan-shaped brooms or brushes. The dust in the trough area consists of major amounts of a dusting agent such as either talc or mica and minor amounts of an X-ray fluorescable material such as either barium sulfate or manganese dioxide or mixtures thereof.

The thus-formed coated membrane can subsequently be irradiated with irradiation which causes the labelling material to fluoresce. The specific wavelength or energy of the radiation emitted by the labelling material can be detected and measured by suitable instrumentation, such as by a spectrometer. The emitted fluoresce will be limited to a particular wavelength or energy which are characteristic of the elements in the labelling material. By recording the type of labelling material or combination of labelling material utilized during the production step of the membrane of the present invention, the fluorescence emission data provides a positive identification of a variety of production parameters, including producing company and plant and year and date of production. The concentration of labelling material or materials can also be related to production factors, dates, or plant location.

In a second (although less preferred) embodiment of the present invention, the labelling material is admixed in a conventional mixer, such as Banbury mixer, with the desired compounding ingredients to form a rubbery composition from which a roofing membrane may be subsequently prepared in sheet form by methods heretofore described. The membrane of this second embodiment is therefore formed from a composition comprising roofing membrane material having a labelling material dispersed therein to form a roofing material composition. The roofing membrane composition generally comprises from about 0.15 to about 1.50 wt. % based upon the weight of roofing membrane material, and preferably from about 0.30 to about 0.75 wt. %.

The process for identifying the roofing membrane of this second embodiment differs from that employed for the first preferred embodiment. Specifically, an ashing step is employed prior to the irradiation step whereby a portion of the material is ashed in a muffle furnace at temperatures within the range of from about 600° to 650° F. The identification process therefore includes ashing a portion of the membrane followed by irradiating the ashed membrane with irradiation which causes the labelling material to fluoresce. Ashing is best described as a controlled thermal oxidation wherein the carbonaceous components are removed while retaining inorganic constituents as non-volatile oxides. The rate of heating is critical for rubber compounds to prevent loss of inorganic components when the carbonaceous components such as oils volatilize or burn. Due to the ashing step, the identification process is considered to be a destructive testing procedure.

Ashed samples may then be prepared for analysis by X-ray fluoresence spectroscopy, from which the spectra for barium and manganese can be determined. Conventional energy dispersive or wavelength dispersive X-ray spectrometers can be used. Instruments which incorporate these spectrometers, such as scanning electron microscopes or electron microprobes, can be employed. The selection of suitable detection means is well within the ability of one skilled in the art.

As in the identification process disclosed for the first embodiment, the irradiation of the fluorescable material produces a fluorescence which is characteristic of the chosen fluorescable material. If either barium sulfate or manganese dioxide are utilized, X-rays are the preferred radiation. Detection and measurement of the fluorescence by a suitable means, such as an energy dispersive X-ray spectrometer, provides identification of production parameters relating to the roofing membrane, when the fluorescence data is compared to corresponding information recorded during the production sequence pertaining to the utilized labelling material.

The roofing compositions of the present invention may additionally contain various conventional compounding and vulcanizing ingredients. Thus, the compositions may contain fillers, processing or softening oils (i.e., plasticizers), antioxidants, antiozonants, UV stabilizers, vulcanizing agents, vulcanizing accelerators, cure retarders, processing aids, tackifying resins, flame retardants and the like.

Fillers which may be utilized include carbon black, bituminous coal fines, silica, silicates, clay, talc, mica, calcium carbonate and the like. Mixtures of such fillers may also be employed.

The roofing compositions may contain from about 10 to about 400, preferably from 25 to 250, parts by weight of such fillers or filler mixtures.

Vulcanizing agents which may be utilized include sulfur and sulfur donor curatives. Mixtures of sulfur and sulfur donor curatives may also be utilized and such mixtures are in most instances preferred. Sulfur donor curatives which may be employed in the compositions include thiuram polysulfides such as tetramethylthiuram disulfide, tetraethylthiuram disulfide, diisopropylthiuram disulfide, tetrabutylthiuram disulfide, dipentamethylenethiuram tetrasulfide, dipentamethylenethiuram hexasulfide, dicyclohexamethylenethiuram disulfide, phenylethylthiuram disulfide and the like; and salts of dialkyldithiocarbamates such as zinc dibutyldithiocarbamate, zinc dimethyldithiocarbamate, zinc diethyldithiocarbamate, bismuth dimethyldithiocarbamate, nickel dibutyldithiocarbamate, copper dimethyldithiocarbamate, selenium diethyldithiocarbamate, lead dimethyldithiocarbamate, tellurium dimethyldithiocarbamate, tellurium diethyldithiocarbamate, cadmium diethyldithiocarbamate and the like. It should be appreciated that this list is not exclusive and other sulfur donor compounds known in the art may be utilized.

The amounts of sulfur, sulfur donor curatives or mixtures thereof employed in the compositions are generally conventional and may range from about 0.5 to about 6.0 parts by weight, with preferred amounts ranging from 1.0 to 4.0 parts by weight, based on the total weight of the composition.

In addition to the sulfur or sulfur donor vulcanizing agents, one or more vulcanizing accelerators may be included in such compositions. Vulcanizing accelerators which may be employed include thioureas such as ethylene thiourea, N.N'-dibutylthiourea, N,N'-diethylthiourea and the like; thiuram monosulfides such as tetramethylthiuram monosulfide, tetraethylthiuram inonosulfide, tetrabutylthiuram monosulfide and the like; benzothiazole sulfenamides such as N-oxydiethylene benzothiazole-2-sulfenamide, N-cyclohexyl benzothiazole-2-sulfenamide, N,N-diisopropyl benzothiazole-2-sulfenamide, N-tert-butyl benzothiazole-2-sulfenamide and the like; 2-mercaptoimidazoline; N,N-diphenyl-guanidine; N,N'-di(2-methylphenyl) guanidine; 2-mercaptobenzothiazole, 2-(morpholinodithio)benzothiazole disulfide and zinc 2-mercaptobenzothiazole.

The vulcanizable elastomeric composition used in the manufacture of roof sheeting or flashing may be prepared by mixing the ingredients of the composition in an internal mixer, for example, a Banbury mixer, an extruder and/or a two-roll mill. In the type B Banbury internal mixer, the dry or powdery materials are added rapidly followed by the addition of any liquids, e.g., process oils, plasticizers, etc. and finally the elastomers. This type of mixing is often referred to as an upside-down mixing technique.

The roofing compositions may be prepared in sheet form in a known manner by calendering or extrusion and then cutting the sheet to desired dimensions. The roofing material will generally be employed in sheet-form, with the sheet having a thickness in the range of from about 0.02 to 0.125 inches.

The sheets may be cut for use as roof sheeting or flashing. Roof sheeting membranes and roof flashing are manufactured from rubber compounds and are typically evaluated for physical properties using test methods developed for mechanical rubber goods. Typical properties include tensile strength, modulus, ultimate elongation, tear resistance, ozone resistance, water absorption and hardness.

The following examples demonstrate the incorporation of X-ray fluorescable labelling material within rubber products.

EXAMPLES

Five samples of an EPDM roofing membrane of conventional composition were prepared which include 1–5 phr $MnO_2$ in 1 phr increments. Each sample was ashed, and the ash analyzed by energy dispersive X-ray (EDX) fluorescence spectroscopy in a scanning electron microscope. The EDX peaks for Mn were linearly proportional to the amount of $MnO_2$ originally incorporated in the sample. Even at 1 phr, the Mn emission peak was 6 times greater than the background (S/N=6), demonstrating the ease of detection of $MnO_2$ at levels considerably below 1 phr. Samples of EPDM roofing membrane stock containing 0.25, 0.50, and 0.75 phr $MnO_2$ were also ashed, then analyzed by EDX to assess the lower limit of detectability. For the lowest level of 0.25 phr, the Mn signal to noise ratio was 1.59, demonstrating that the Mn peak is readily observable above the background noise.

Five samples of EPDM roofing membrane of the same conventional composition described above were prepared to contain 1–5 phr $BaSO_4$ in 1 phr increments. A control without $BaSO_4$ was also prepared. Each cured sample was ashed, then analyzed by EDX. The barium X-ray emission peaks were observed to be a linear function of the amount of $BaSO_4$ that had been added to the roofing membrane compound. Even at 1 phr, the barium signal was more than three times the background noise (S/N>3). The lower limit of $BaSO_4$ detection was investigated by incorporating 0.25, 0.50, and 0.75 $BaSO_4$ in EPDM roofing membrane stock. The ash of all three samples was analyzed by EDX in the scanning electron microscope. A signal to noise ratio (S/N) of 0.95 similarly indicates the ease of observing such small levels of this X-ray fluorescable labelling material.

The following examples illustrate the incorporation of X-ray fluorescable labelling materials in dusting agents used on rubber products.

Barium sulfate was mixed with mica to give a dusting agent containing 5% and 10% $BaSO_4$ by weight. Manganese dioxide was also mixed with mica to give a dusting agent with 5% and 10% $MnO_2$ by weight. Finally, both barium sulfate and manganese dioxide were mixed with mica to produce a dusting agent containing 5% of each labelling material by weight. These dusting agent blends were analyzed by EDX spectroscopy. Pronounced emission peaks for Al, Si, Mg, K, and Fe from the mica were detected. Moderate signals were also observed for Ba and S when analyzing the 5% and 10% $BaSO_4$ dusting agents. At 10% $BaSO_4$, the signal for barium was 4.3 times greater than the background noise. At 5% the S/N ratio was 2.0. In both cases, the Ba emission peak was readily observable above the continuous X-radiation. With 5% and 10% $MnO_2$ in the mica dusting agent, the Mn peak was also readily observable with S/N ratios of 2.2 and 3.9, respectively.

For mica containing both $BaSO_4$ and $MnO_2$ at 5% levels, both the Ba and Mn could be seen with ease. The S/N ratios were 2.8 and 1.4, respectively.

While the composition and membrane of the present invention have been described in detail, it is to be understood that various modifications and changes that do not depart from the spirit and scope of the present invention may be made. For example, the roofing membrane and the roofing composition may be employed in the closely related functions of roof flashing or sheeting. In these functions, the membrane covers roof protrusions, drains, gutters, outlets, edge trims, parapet wall terminations, corners and other roof details. Also, various combinations and arrangements of labelling materials may be employed to provide a distinctive and individual fluorescence emission.

What is claimed is:

1. A method of analyzing an identifiable rubber article comprised of a rubber-based material and an X-ray fluorescable material, comprising the steps of irradiating the material with a fluorescence-inducing wavelength and analyzing the fluorescence emission data of said material.

2. The method of claim 1 wherein said rubber article comprises a rubber roofing membrane or material.

3. The method of claim 2 comprised of an EPDM terpolymer.

4. The method of claim 1 wherein said X-ray fluorescable material is selected from the group consisting of manganese dioxide and barium sulfate, and mixtures thereof.

5. The method of claim 1 wherein said X-ray fluorescable material is in particulate form.

6. The method of claim 4 wherein said X-ray fluorescable material comprises from about 0.25 to about 0.75 parts per 100 parts by weight of said rubber-based material and said X-ray fluorescable material.

7. The method of claim 2 wherein said roofing membrane is in sheet form, said sheet including over at least a portion of at least one surface thereof a dusting agent coating containing an X-ray fluorescable material.

8. The method of claim 7 comprised of an EPDM terpolymer.

9. The method of claim 7 wherein said X-ray fluorescable material is selected from the group consisting of manganese dioxide and barium sulfate, and mixtures thereof.

10. The method of claim 7 wherein said X-ray fluorescable material is in particulate form.

11. The method of claim 7 wherein said X-ray fluorescable material comprises from about 5 to about 10 weight percent of said coating.

12. The method of claim 7 wherein said material is in the form of a cured sheet membrane.

13. The method of claim 7 wherein said material is in the form of a vulcanizable flashing material.

14. The method of claim 7 wherein said material is in the form of a non-vulcanizing flashing material.

* * * * *